United States Patent [19]
Ragazzi

[11] Patent Number: 5,306,265
[45] Date of Patent: Apr. 26, 1994

[54] SAMPLING AND INFUSION CONNECTOR FOR AN EXTRACORPOREAL BLOOD CIRCULATION LINE

[75] Inventor: Guido Ragazzi, Massa Finalese, Italy
[73] Assignee: Hospal, Ltd., Basel, Switzerland
[21] Appl. No.: 989,149
[22] Filed: Dec. 11, 1992

[30] Foreign Application Priority Data
Dec. 13, 1991 [IT] Italy ............ TO91A000975

[51] Int. Cl.⁵ .................................. A61M 25/00
[52] U.S. Cl. ............................. 604/283; 604/284;
  417/151; 285/177; 128/912
[58] Field of Search ................ 604/283, 284, 905;
  417/63, 151; 128/911, 912; 23/863.81, 863.85;
  285/177; D17/63, 151

[56] References Cited
U.S. PATENT DOCUMENTS
3,776,042 12/1973 Werra et al. .............. 73/863.85
4,838,873 6/1989 Landskron et al. ............ 604/905
5,221,271 6/1993 Nicholson et al. ............ 604/293

FOREIGN PATENT DOCUMENTS
8900867 2/1989 PCT Int'l Appl. .
1560673 2/1980 United Kingdom .
990583 4/1985 United Kingdom .

*Primary Examiner*—Jerome L. Kruter
*Attorney, Agent, or Firm*—Finnegan, Henderson, Farabow, Garrett & Dunner

[57] ABSTRACT

A connector includes a body having a tubular cavity connected to two ducts and includes an infusion aperture for infusing a liquid into the line and a sampling aperture for sampling blood. A constriction having a diameter progressively decreasing towards the inlet aperture is disposed in the cavity between the two apertures and produces a Venturi tube effect, preventing the sampled blood from being affected by the infused liquid.

10 Claims, 1 Drawing Sheet

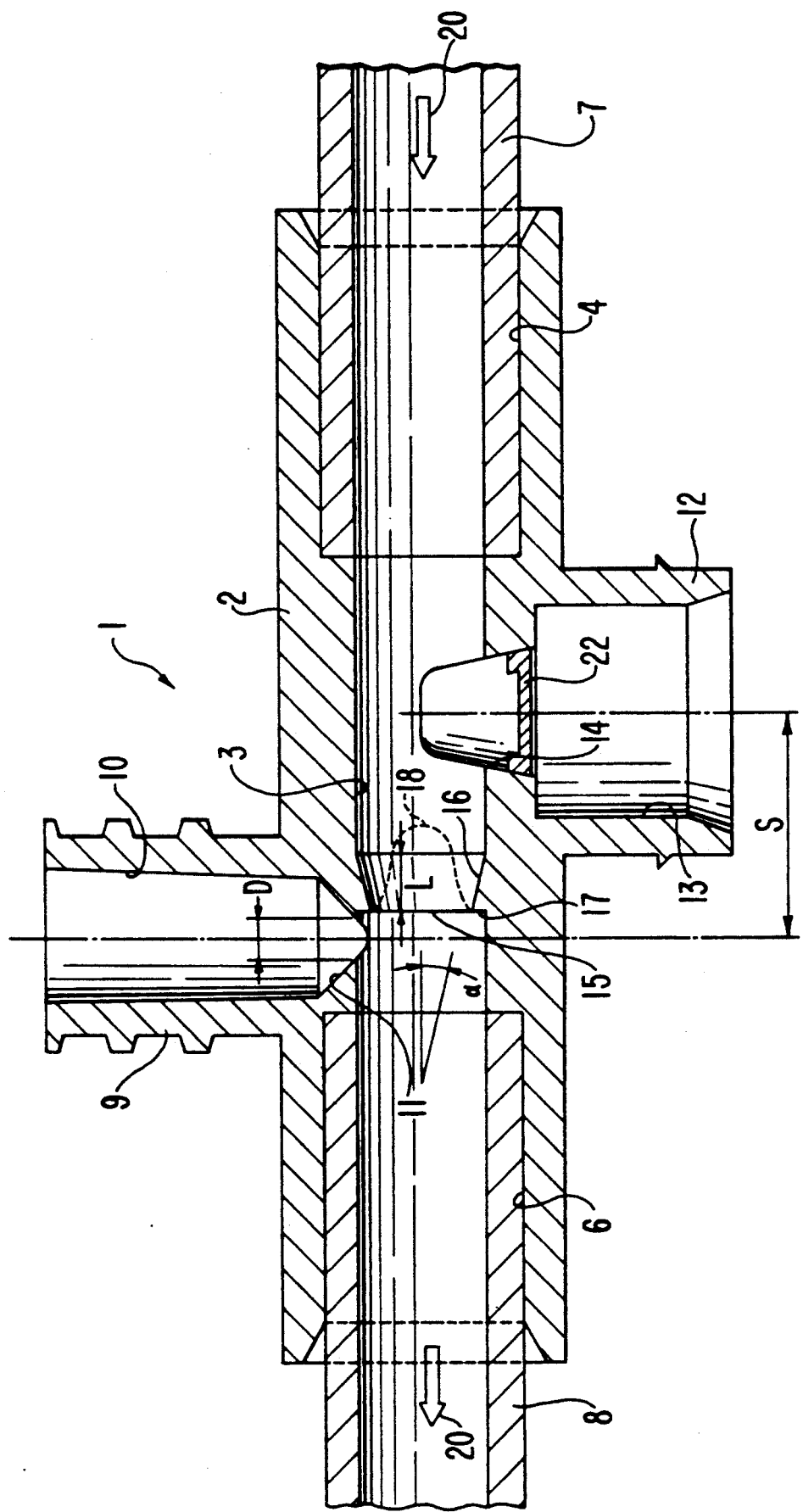

SAMPLING AND INFUSION CONNECTOR FOR AN EXTRACORPOREAL BLOOD CIRCULATION LINE

BACKGROUND OF THE INVENTION

1. Field of the Invention

The invention relates to a sampling and infusion connector for an extracorporeal blood circulation line.

2. Description of the Related Art

As is known, lines for circulating blood outside the body, such as those used in a dialysis apparatus, need at least one connector for attachment to a blood line, the connector having a port for sampling blood and/or for infusing liquids into the blood flow. The flow is controlled by a pump, preferably peristaltic, which acts via rollers or the like on a flexible duct portion of the line.

A known connector for an aforementioned line comprises a tubular body having a blood inlet, an infusion opening, and a sampling opening located between the blood inlet and the infusion opening, the sampling opening for permitting test quantities of blood to be withdrawn such as through a syringe. This related art arrangement has the disadvantage that, during sampling, the infusion liquid tends to be sucked back in countercurrent by the negative pressure caused by the sampling syringe, thereby mixing with the sampled blood and altering its composition.

Thus, in the related art, in order to prevent the infusion liquid from reaching the sampling aperture at the moment when suction is exerted by the syringe, it is necessary to interrupt the infusion process for a period of time, which can cause adverse effects on the treatment. Alternatively, the connector could be constructed so that the sampling aperture is disposed at an appreciable distance from the infusion aperture, in which case the connector would be bulky and inconvenient to use.

SUMMARY OF THE INVENTION

An object of the invention is to provide a connector for an extracorporeal blood circulation line, that is simple and eliminates the previously-listed disadvantages of known connectors.

The object is achieved by providing sampling and infusion connector for an extracorporeal blood circulation line, comprising a body having a tubular cavity, with two ends that are adapted to be connected in the blood circulation line, the body also comprising an infusion opening for introducing a liquid into the tubular cavity, and a sampling opening for removing a test amount of blood from the tubular cavity. The cavity has a constriction disposed between the infusion opening and the sampling opening, the constriction having a diameter which progressively decreases towards the infusion opening.

BRIEF DESCRIPTION OF THE DRAWING

The invention will be more clearly understood from the following description of a preferred embodiment, described by way of example with reference to the accompanying drawing, which is a cross-section of a sampling and infusion connector of the present invention.

DESCRIPTION OF THE PREFERRED EMBODIMENT

Referring to the drawing, the general reference 1 denotes a connector for an extracorporeal blood circulation line. Connector 1 includes a rigid plastics body 2 having a tubular cavity 3. The cavity 3 has two larger-diameter ends 4, 6 which in operation are respectively connected to an inlet duct 7 and an outlet duct 8 for blood, the two ducts forming part of an extracorporeal circulation line (not shown).

During operation, a peristaltic pump acts on a portion (not shown) of the duct 7 and causes blood to flow by compressing the aforementioned portion and thus producing a substantially sinusoidally pulsating flow.

The body 2 is integrally connected with a sleeve 9 which has a slightly conical cavity 10 with its axis perpendicular to the axis of the tubular cavity 3. The cavity 10 communicates with the cavity 3 of body 2 via an infusion aperture 11 which has a strongly conical surface, such that its diameter D, at the intersection with cavity 3, is about a third of the diameter of cavity 10. Sleeve 9 has an external thread for firmly connecting to an infusion tube system (not shown).

Body 2 is also integrally connected with a sleeve 12 disposed upstream of sleeve 9 relative to the direction of flow of the blood. Sleeve 12 has a substantially cylindrical cavity 13, and also has an axis perpendicular to the axis of the tubular cavity 3, sleeve 12 extending in the opposite direction from sleeve 9. Cavity 13 communicates with cavity 3 of body 2 via a sampling opening 14 having a slightly conical surface. The sleeve 12 has conventional securing means for connecting a plug 22 of resiliently deformable material, adapted to be perforated by a syringe during operation.

According to the invention cavity 3 of body 2 is formed with a constriction (general reference 15) disposed between apertures 11 and 14 and having a diameter which decreases towards the infusion aperture 11. The constriction 15 thus constitutes a portion of a Venturi tube, e.g., a half thereof. More particularly the constriction 15 has a frusto-conical surface 16, the minor base of which is disposed immediately upstream of the infusion opening 11. The surface 16 and the cavity 3 forms a step 17 which can advantageously be a flat orthogonal annular surface substantially in line with the edge of the aperture 11 of diameter D.

The surface 16 slopes relative to the axis of cavity 3 by an angle α of between 10° and 20°, preferably 15°. The length L of the constriction surface 16 is chosen to produce a step 17 having a height of between 1/10 and 3/10 the diameter of cavity 3. The distance S between the axes of the two cavities 10, 13 of the sleeves 9, 12 is between one and three times the diameter of the cavity 3 of body 2. Advantageously, when the diameter of cavity 3 is 4.2 mm, the distance S can be chosen equal to 8 mm, whereas the height of step 17 can be chosen equal to 0.5 mm.

In operation, connector 1 operates as follows. When the extracorporeal circulation line is in operation, the peristaltic pump drives blood through cavity 3 of body 2 in the direction indicated by arrows 20. Infusion liquid is introduced into the line through sleeve 9 and the infusion opening 11. A Venturi tube effect, i.e., a negative pressure, is produced opposite the constriction 15 and helps to draw the infusion liquid through the opening 11 and mix it with the blood from duct 7.

When circulating blood has to be sampled, the blood is removed by inserting the needle of a syringe through the sleeve 12, opening 14, and plug 22, thereby causing a negative pressure in the region upstream of the constriction 15. However, the step 17 and the negative pressure resulting from the Venturi effect prevent the infusion liquid from spreading in the blood upstream of the step 17, and consequently the blood sampled by the syringe is not mixed with the infusion liquid.

At the moment in which the peristaltic pump temporarily stops, thus slowing the flow in the line, the infusion liquid may be caused to diffuse towards the sampling opening 14. However, the distance S and the height of step 17, when dimensioned as previously stated, reliably hinder such diffusion by limiting it to a region 18 indicated by a curved chain line in the drawing.

The preceding clearly shows the advantages of the connector according to the invention compared with known connectors. The connector prevents sampled blood to become mixed with infusion liquid. Also the distance S is reduced to a minimum, so that the complete connector 1 is very compact.

Of course various modifications and improvements can be made to connector 1, without departing from the scope or spirit of the invention. For example, the constriction 15 can have a curved instead of a straight generatrix, thus avoiding the sharp corner between surface 16 and the surface of cavity 3. Thus, it is intended that the previous description of the invention is exemplary and explanatory only, with a true scope and spirit of the invention being defined by the following claims.

What is claimed is:

1. A sampling and infusion connector for an extracorporeal blood circulation line, the connector comprising:
    a body having upstream and downstream distal ends and an elongated cavity extending therebetween, the upstream and downstream ends for connection to ducts of the extracorporeal blood circulation line;
    infusion port means connected to the elongated cavity for introducing a substance into the cavity;
    sampling port means connected to the cavity for removing blood from the cavity; and
    means disposed in the cavity between the infusion port means and the sampling port means for preventing the substance introduced through the infusion port means from entering the sampling port means, the preventing means including a constriction having a diameter that progressively decreases towards the infusion opening.

2. A connector according to claim 1, wherein the constriction includes at least a part of a Venturi tube.

3. A connector according to claim 1, wherein the constriction includes a frusto-conical surface, with a minor base substantially in line with an edge of the infusion port means.

4. A connector according to claim 3, wherein the frusto-conical surface is inclined at an angle $\alpha$ of between 10° and 20° relative to an axis of the cavity.

5. A connector according to claim 4, wherein the cavity has a minor base that forms a step having a height of between 1/10 and 3/10 of a diameter of the cavity.

6. A connector according to claim 1, wherein the infusion port means and the sampling port means include a pair of diametrically opposed sleeves integrally connected to the body, the cavity and each of the sleeves including an axis, the axes of the sleeves being substantially perpendicular to the axis of the cavity.

7. A connector according to claim 6, wherein a distance (S) between the axes of the sleeves is between one and three times a diameter of the cavity.

8. A connector according to claim 1, wherein the sampling port means includes a plug constructed of resiliently deformable material, and to be perforated by a needle of a syringe.

9. A connector according to claim 1, wherein the sampling port means includes a plug constructed of resiliently deformable material, and adapted to be perforated by a needle of a syringe.

10. A sampling and infusion connector for an extracorporeal blood circulation line, the connector comprising:
    a body having upstream and downstream distal ends and an elongated cavity extending therebetween, the upstream and downstream ends for connection to ducts of the extracorporeal blood circulation line;
    an infusion port connected to the elongated cavity for introducing a substance into the cavity;
    a sampling port connected to the cavity for removing blood from the cavity; and
    a constriction disposed in the cavity between the infusion port and the sampling port preventing the substance introduced through the infusion port from entering the sampling port, the constriction having a diameter that progressively decreases towards the infusion port.

* * * * *